US011795617B2

(12) United States Patent
Menke et al.

(10) Patent No.: US 11,795,617 B2
(45) Date of Patent: Oct. 24, 2023

(54) METHOD AND APPARATUS FOR DRYING PREFERABLY A MOVING MATERIAL WEB BY MEANS OF AT LEAST ONE DRYING DEVICE HEATED BY MEANS OF BIOGAS AND COMPRISING INFRARED RADIATORS

(71) Applicants: Meri Environmental Solutions GmbH, Munich (DE); Voith Patent GmbH, Heidenheim (DE)

(72) Inventors: Lucas Menke, Munich (DE); George Troubounis, Munich (DE); Henning Laubrock, Munich (DE); Philipp Kückmann, Mönchengladbach (DE)

(73) Assignees: Meri Environmental Solutions GmbH, Munich (DE); Voith Patent GmbH, Heidenheim (DE)

( * ) Notice: Subject to any disclaimer, the term of this patent is extended or adjusted under 35 U.S.C. 154(b) by 589 days.

(21) Appl. No.: 17/055,556

(22) PCT Filed: May 8, 2019

(86) PCT No.: PCT/EP2019/061853
§ 371 (c)(1),
(2) Date: Nov. 13, 2020

(87) PCT Pub. No.: WO2019/219484
PCT Pub. Date: Nov. 21, 2019

(65) Prior Publication Data
US 2021/0198847 A1 Jul. 1, 2021

(30) Foreign Application Priority Data
May 16, 2018 (DE) .............. 10 2018 003 969.3

(51) Int. Cl.
*D21F 5/00* (2006.01)
*C02F 3/28* (2023.01)
*C12M 1/107* (2006.01)

(52) U.S. Cl.
CPC .............. *D21F 5/002* (2013.01); *C02F 3/28* (2013.01); *C12M 1/107* (2013.01); *C02F 2101/40* (2013.01)

(58) Field of Classification Search
CPC ......... C10J 3/84; C10J 3/57; C10J 3/78; C10J 2200/09; C10J 2200/152; C10J 2300/0946;
(Continued)

(56) References Cited

U.S. PATENT DOCUMENTS 5,090,898 A * 2/1992 Smith .................. F24C 3/042
431/328
5,553,391 A 9/1996 Bakalar
(Continued)

FOREIGN PATENT DOCUMENTS

AT 505932 A4 5/2009
CN 101838952 A 9/2010
(Continued)

OTHER PUBLICATIONS

English translation of the International Search Report in International Application No. PCT/EP2019/061853, dated Jul. 18, 2019.
(Continued)

*Primary Examiner* — David J Laux
(74) *Attorney, Agent, or Firm* — Hershkovitz & Associates, PLLC; Abe Hershkovitz; Eugene C. Rzucidlo

(57) ABSTRACT

A method for producing an object, wherein the method comprises drying the object or a primary product thereof, the object or a primary product thereof being at least partially dried in at least one drying device, wherein at least one of the at least one drying units contains at least one infrared radiator which is at least partially heated by means of biogas, a combustion gas selected from the group consisting of oxygen, air or other oxygen-containing gases is added to the biogas before said biogas is supplied to the at least one infrared radiator in order to heat said at least one infrared radiator, and the oxygen content in the waste gas resulting from the at least one infrared radiator being heated by means
(Continued)

Figure 1:
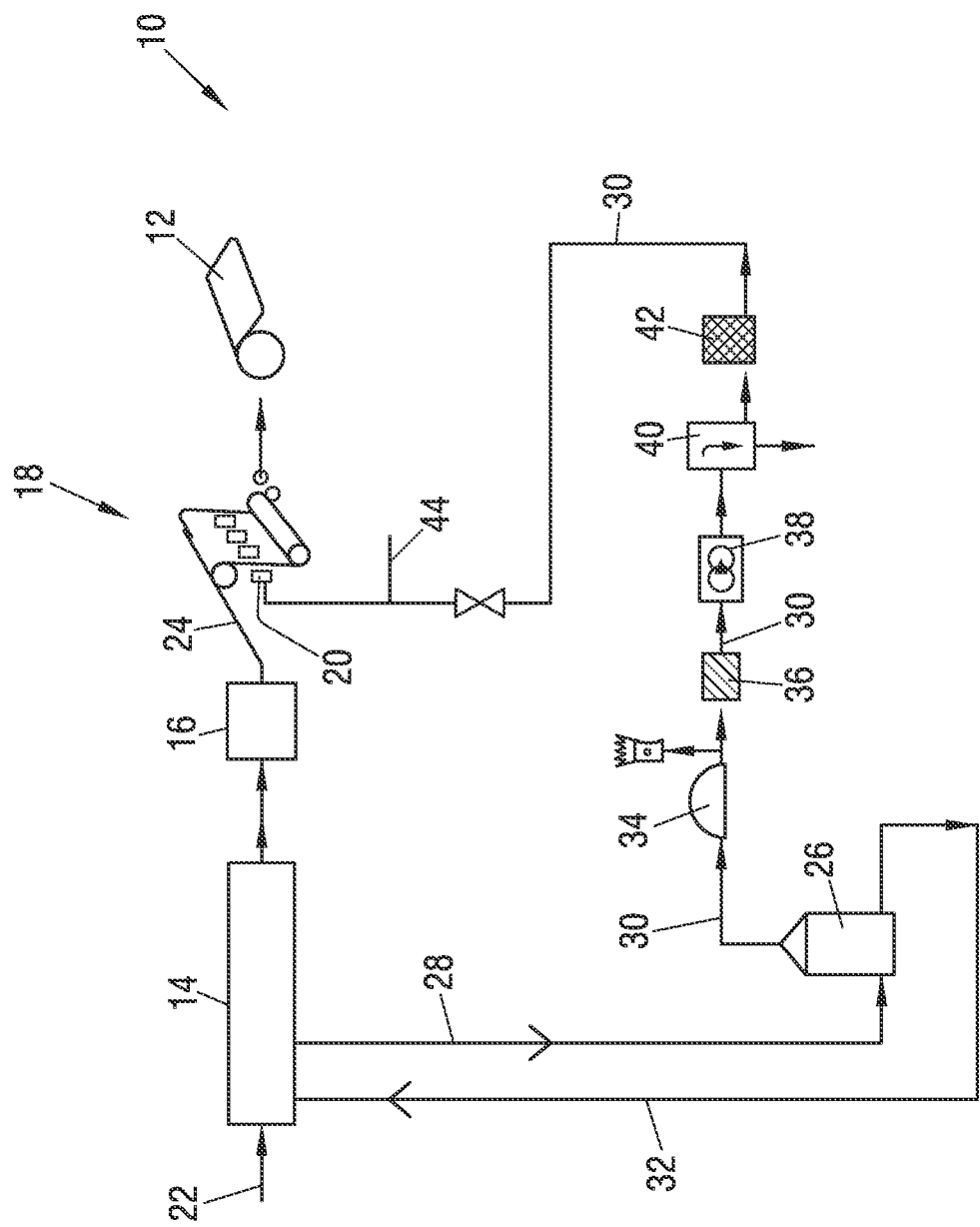

of the biogas is measured by means of a measuring device and the amount of combustion gas added to the biogas.

20 Claims, 2 Drawing Sheets

(58) Field of Classification Search
CPC ........ C10J 2300/1246; C10J 2300/1807; C10J 2300/0903; C10J 2300/0906; C10J 2300/0909; C10J 3/86; C01B 3/02; C21B 13/0026; C21B 13/0073; C21B 13/008; C21B 13/10; C21B 2200/00
See application file for complete search history.

(56) References Cited

U.S. PATENT DOCUMENTS

| | | | |
|---|---|---|---|
| 5,966,835 | A | 10/1999 | Bakalar |
| 6,478,963 | B1 | 11/2002 | Rossmanith |
| 6,560,893 | B1 | 5/2003 | Bakalar |
| 2001/0011457 | A1* | 8/2001 | Shishido ............... C10K 1/02 60/614 |
| 2003/0051369 | A1 | 3/2003 | Aust |
| 2011/0146155 | A1* | 6/2011 | Bentzen ............... C10K 1/101 48/89 |
| 2013/0209338 | A1* | 8/2013 | Prasad ............... C01B 7/07 422/105 |
| 2013/0291834 | A1 | 11/2013 | Diehl et al. |
| 2013/0302217 | A1* | 11/2013 | Lesueur ............... F27B 14/12 422/198 |
| 2015/0052812 | A1* | 2/2015 | Scalzo ............... C10L 1/04 48/197 FM |

FOREIGN PATENT DOCUMENTS

| | | |
|---|---|---|
| CN | 202390419 U | 8/2012 |
| CN | 102977962 A | 3/2013 |
| DE | 10340074 A1 | 3/2005 |
| DE | 102005056336 A1 | 5/2007 |
| DE | 102010062198 A1 | 5/2012 |
| EP | 0170332 A1 | 2/1986 |
| EP | 0539430 B1 | 10/1994 |
| EP | 1071636 B1 | 1/2002 |
| EP | 1295987 A2 | 3/2003 |
| EP | 3296556 A1 | 3/2018 |
| WO | 9951532 A1 | 10/1999 |

OTHER PUBLICATIONS

Office Action in related German Application No. DE 10 2018 003 969, dated Dec. 20, 2018.
English translation of the International Preliminary Report on Patentability in International Application No. PCT/EP2019/061853, dated Nov. 26, 2020.
Machine-generated English language translation of Description of EP 1295987 A2 (Mar. 26, 2003).
English language Abstract of DE 10340074 A1 (Mar. 31, 2005).
Machine-generated English language translation of Description of DE 102010062198 A1 (May 31, 2012).
Machine-generated English language translation of Description of EP 1071636 B1 (Jan. 30, 2002).
Machine English language translation of Description of CN 101838952 A (Sep. 22, 2010).
English language Abstract of AT 505932 A4 (May 15, 2009).
English language Abstract of DE 102005056336 A1 (May 31, 2007).
English language Abstract of CN 102 977 962 A (Mar. 20, 2013).
English language Abstract of CN 202 390 419 U (Aug. 22, 2012).

* cited by examiner

METHOD AND APPARATUS FOR DRYING PREFERABLY A MOVING MATERIAL WEB BY MEANS OF AT LEAST ONE DRYING DEVICE HEATED BY MEANS OF BIOGAS AND COMPRISING INFRARED RADIATORS

The present invention relates to a method for producing an object, such as in particular a moving material web, such as a coated paper or cardboard web, the method comprising drying the object or a primary product thereof by means of at least one drying device which comprises one or more infrared radiators. In addition, the present invention relates to an apparatus which is particularly suitable for carrying out the method.

There is a wide range of methods, in particular continuous methods, for producing an object in which the object or a primary product thereof is dried by means of one or more drying devices, such as those comprising one or more infrared radiators. An example of such a method is the production of material webs such as paper, cardboard or tissue webs, and in particular coated paper or cardboard webs. Coated paper is a paper of which the surface has been finished with a binding agent layer or coating, for example to give the paper a more closed, smoother and/or more stable surface, in order to increase its ability to reproduce details and achieve better quality during printing, for example. The coating is applied to the paper as a thin liquid film, before the paper that has been coated in this manner is subsequently dried. For example, EP 1 295 987 A2 discloses such a method for drying a coated paper or cardboard web, in which the web is first pre-dried in an infrared dryer comprising infrared radiators and then dried further by means of air in an air dryer, the air dryer being operated such that the heat transfer coefficient between the drying air and the web increases in the movement direction of the web.

Infrared radiators are usually heated electrically or by means of natural gas. However, the operating costs are very high, especially for electrically heated infrared radiators. For this reason, infrared radiators are primarily heated by means of natural gas in corresponding large-scale processes. The same also applies to air dryers, which are often supplied with natural gas as the primary energy source or with a secondary source, such as steam. However, the operating costs are also very high for both types of drying and amount to 15 to 20% of the total operating costs, for example, in the case of methods for producing coated paper.

The object of the present invention is therefore that of providing a method for producing an object, such as in particular a moving material web, such as a coated paper or cardboard web, which comprises drying the object or a primary product thereof by means of at least one drying device comprising at least one infrared radiator, and in which the operating costs, and in particular the operating costs associated with the drying by means of the at least one drying device, are considerably reduced, and yet a specified degree of dryness of the object is still precisely achieved.

According to the invention, this object is achieved by a method for producing an object, such as in particular a moving material web, such as a coated paper or cardboard web, wherein the method comprises drying the object or a primary product thereof, the object or a primary product thereof being at least partially dried in at least one drying device, wherein at least one of the at least one drying devices contains at least one infrared radiator which is at least partially heated by means of biogas, a combustion gas selected from the group consisting of oxygen, air or other oxygen-containing gases is added to the biogas before said biogas is supplied to the at least one infrared radiator in order to heat said at least one infrared radiator, and the oxygen content in the waste gas resulting from the at least one infrared radiator being heated by means of the biogas is measured by means of a measuring device and the amount of combustion gas added to the biogas before said biogas is supplied to the at least one infrared radiator is controlled on the basis of the measured oxygen content.

The operating costs associated with the drying by means of the drying device can be reduced by the one or more infrared radiators used for the drying process in the drying device not being heated electrically or by means of natural gas, but rather by means of biogas. This is because biogas, such as in particular methane-containing biogas, is cheaper to obtain than natural gas, particularly if the biogas is produced close to the drying device, and very particularly if the biogas is produced in the same facility as waste products from the method, since at least some of the costs for waste disposal can be saved in this case. These cost advantages are achieved to a particularly high degree if all of the drying devices used each comprise one or more infrared radiators and all of the infrared radiators are heated completely by means of biogas which preferably contains methane. In this context, biogas is understood to be a combustible gas that is generated by processing biomass of any type, for example by microorganisms which convert biomass, such as organic contaminants, into methane or other combustible substances.

As explained, the method according to the invention results in a considerable cost saving by comparison with that known from the prior art particularly if the biogas used to heat the drying device is produced in the same facility in which the method for producing and drying the object is carried out, specifically preferably from waste products generated during the method itself. The infrastructure for supplying natural gas can thereby be dispensed with and the costly disposal of the generated waste products can be completely or at least partially dispensed with, as a result of the waste products being used to generate the biogas.

A distinguishing feature of the drying unit used is that it brings about energy and mass transfer within the item to be dried. The energy transfer can occur through contact, convection and/or electromagnetic radiation, the liquid phase of the item to be dried partially changing its state of aggregation and leaving the item. In this case, the biogas can be used to heat the drying unit as a primary energy source, but alternatively also via the further step of providing a secondary energy flow, such as steam.

According to the invention, one or more of the drying devices which are at least partially heated by means of biogas each contain one or more infrared radiators, at least one, preferably all, of the infrared radiators being at least partially heated by means of biogas. Each drying device preferably comprises one or more infrared radiators, all infrared radiators being heated completely by means of biogas.

According to a preferred embodiment of the present invention, waste water and/or some other residual product is also generated during the method, the biogas, which preferably contains methane, being produced by treating the generated waste water and/or other residual product. This can be easily achieved, for example, in the production of paper, cardboard or tissue webs, such as coated paper or cardboard webs, since these methods produce considerable amounts of organically polluted waste water, which, in most existing facilities, is cleaned using reactors that contain anaerobic microorganisms. During purification by means of anaerobic microorganisms, the organic contaminants are converted into a biogas that contains methane and carbon dioxide, which biogas is mostly disposed of, without having been used, in existing facilities. According to the present invention, this biogas can be used to heat the infrared radiators used in the drying device for drying the paper, cardboard or tissue webs. The same can also be achieved, for example, in the production of potato chips, in which a considerable amount of biomass waste is produced by the potato peel, which biomass waste can easily be converted into methane-containing biogas via fermentation.

Alternatively or additionally, for the same purpose, process water can be circulated during the method, which water becomes contaminated with organic compounds, for example, during the method, the biogas, in particular methane-containing biogas, being produced by treating the generated process water. This can also be easily achieved in the production of paper, cardboard or tissue webs, such as coated paper or cardboard webs, since considerable amounts of process water are circulated during these methods, the process water becoming contaminated with organic compounds during the method. This process water has to be cleaned in existing facilities and is already cleaned on a large scale using reactors that contain anaerobic microorganisms. As explained, the organic contaminants are in this case converted into a biogas that contains methane and carbon dioxide, which biogas is mostly disposed of, without having been used, in existing facilities.

For the reasons set out above, it is therefore particularly preferable according to the present invention for waste water to be generated and/or for process water to be circulated during the method, which process water becomes contaminated with organic compounds, for example, during the method, the treatment of the waste water and/or process water being carried out in a reactor containing anaerobic microorganisms, the anaerobic microorganisms converting organic compounds contained in the waste water and/or process water into a methane-containing biogas. As explained, this embodiment can be implemented particularly easily in the production of paper, cardboard or tissue webs, such as coated paper or cardboard webs.

All types of anaerobic reactors known to a person skilled in the art can be used as anaerobic reactors filled with anaerobic microorganisms, for example contact sludge reactors, UASB reactors, EGSB reactors, fixed bed reactors and fluidized bed reactors, with good results being achieved in particular with UASB reactors and EGSB reactors. In the case of UASB and EGSB reactors, waste water to be cleaned is usually supplied continuously to the reactor via an inlet in the lower reactor region, and said water is passed through a sludge bed which is positioned above the inlet and contains microorganism pellets. When the organic compounds from the waste water are degraded, the microorganisms form biogas that contains methane and carbon dioxide in particular, some of which biogas accumulates on the microorganism pellets in the form of small bubbles and some of which rises upward in the reactor in the form of free gas bubbles. As a result of the accumulated gas bubbles, the specific weight of the pellets decreases, as a result of which the pellets rise upward in the reactor. In order to separate the formed biogas and the rising pellets from the water, separators are typically arranged in the middle and/or upper part of the reactor, usually in the form of gas hoods, under the ridge of which biogas collects, which forms a gas cushion, under which a flotation layer of microorganism pellets and waste water is located. Cleaned water freed of gas and microorganism pellets rises upward in the reactor and is drawn off at the upper end of the reactor via overflow means, whereas the microorganism pellets freed of the gas bubbles sink downward in the reactor again due to their now increased specific weight. Methods of this kind and corresponding reactors are described, for example, in EP 0 170 332 A1, in EP 1 071 636 B1 and in EP 0 539 430 B1.

According to a particularly preferred embodiment of the present invention, a moving material web, preferably a coated paper or cardboard web, is produced by means of the method according to the invention, and said web is a least partially dried in the at least one drying device, waste water containing organic compounds being produced and/or process water being circulated during the method, which process water becomes contaminated with organic compounds during the method, the biogas being generated by treating the waste water and/or process water in a reactor containing anaerobic microorganisms, the anaerobic microorganisms converting organic compounds contained in the waster water and/or process water into the biogas.

Alternatively, the method according to the invention can also be used in such a way that a residual product other than waste water or contaminated process water is generated during the method, the biogas being produced by fermenting the other residual product that has been generated. This embodiment is suitable, for example, for methods for producing potato chips in which the fried potato chips are dried in a drying device comprising infrared radiators. This method produces a considerable amount of biomass waste in the form of potato peel, which can easily be converted into methane-containing biogas by fermentation.

As explained, the biogas used preferably contains methane, since methane has a high net calorific value and can easily be produced by anaerobic microorganisms as a metabolic end product. The biogas, which is particularly preferably produced in the method itself, as explained, preferably contains at least 50 wt. %, more preferably at least 60 wt. % and very particularly preferably at least 70 wt. %, methane, based on 100 wt. %.

In order to ensure effective combustion of the biogas and, if necessary, remove interfering components, it is proposed in a development of the inventive concept that the biogas be conditioned before being used to heat the at least one infrared radiator, the biogas preferably being subjected to one or more of the following treatment steps for conditioning purposes:
 i) gas drying to remove moisture from the biogas, in order to increase combustibility,
 ii) compression to compress the biogas so that it has a suitable net calorific value per unit of volume,
 iii) desulfurization to remove interfering sulfur-containing compounds, such as in particular hydrogen sulfide,
 iv) cleaning with activated carbon to remove interfering compounds, such as in particular hydrogen sulfide.

According to a further preferred embodiment, the biogas is temporarily stored in a buffer tank before being used to heat the at least one infrared radiator. This is therefore advantageous because biogas can be subject to changes in composition over the production period, such as in particular changes in methane content and amount produced. For example, the degree of contamination of the contaminated waste water and process water produced during paper production fluctuates over time, as a result of which the biogas generated by anaerobic microorganisms when the waste water and process water is cleaned is also subject to changes over time in amount and/or composition, such as changes in methane content. If the methane content of the biogas drops, more biogas has to be used per unit of time to heat the infrared radiators, whereas the amount of biogas required per unit of time to heat the drying device, namely the infrared radiators, is correspondingly lower when the methane content of the biogas increases. Allowances can be made for these fluctuations in the composition of the biogas and/or fluctuations in the amount of biogas generated per unit of time by the biogas being temporarily stored in a buffer tank before being used to heat the at least one infrared radiator, in order to ensure continuous supply of a sufficient amount of biogas to the at least one infrared radiator even with fluctuations in the composition of the biogas and/or fluctuations in the amount of biogas generated.

In order to achieve effective combustion and thus make good use of the net calorific value of the biogas, according to the invention, a combustion gas selected from the group consisting of oxygen, air or other oxygen-containing gases is preferably added to the biogas before said biogas is supplied to the at least one infrared radiator in order to heat said at least one infrared radiator.

In order to achieve optimum combustion in the at least one infrared radiator and thus make use of the net calorific value of the biogas, according to the invention, the oxygen content in the waste gas resulting from the at least one infrared radiator being heated by means of the biogas is measured by means of a sensor, and the amount of combustion gas added to the biogas before said biogas is supplied to the at least one infrared radiator is controlled on the basis of the measured oxygen content. The oxygen content in the waste gas resulting from the at least one infrared radiator being heated by means of the biogas by burning the biogas using the combustion gas in the at least one infrared radiator is measured by means of a measuring device, such as a sensor. A lambda sensor is particularly preferably used as the measuring device. The measuring device or lambda sensor is preferably arranged directly ahead of the at least one infrared radiator in order to set an optimum mixture of biogas and combustion gas so as to prevent both an excess supply of cooling incoming air and carbon monoxide with unused residual calorific value, resulting from a lack of oxygen, in the at least one infrared radiator.

In a development of the inventive concept, the net calorific value of the biogas is determined before said biogas is supplied to the at least one infrared radiator. This can be achieved in all ways known to a person skilled in the art. For example, the gross calorific value can first be determined using a combustion calorimeter before the net calorific value is calculated from the gross calorific value, as is known, by subtracting the enthalpy of vaporization of the water from the gross calorific value.

The amount of biogas to be supplied to the at least one infrared radiator per unit of time is preferably controlled on the basis of the determined net calorific value of the biogas.

In particular, it is preferable for the amount of biogas to be supplied to the at least one infrared radiator per unit of time and the amount of combustion gas to be supplied to the biogas per unit of time to be controlled such that the at least one infrared radiator has a constant heat radiation output.

For example, if, for production-related reasons, the amount of biogas generated in the method is temporarily too low for sufficient heating of the infrared radiators, it may be expedient to add (small amounts of) natural gas to the biogas before said biogas is supplied to the at least one infrared radiator in order to heat said at least one infrared radiator.

Furthermore, if, for production-related reasons, the net calorific value or methane content of the biogas generated in the method is temporarily too low for sufficient heating of the infrared radiators, it may be necessary to add methane to the biogas before said biogas is supplied to the at least one infrared radiator in order to heat said at least one infrared radiator.

The present invention also relates to an apparatus for producing an object, such as in particular a moving material web, such as a coated paper or cardboard web, which is particularly suitable for carrying out the method described above, wherein the apparatus comprises:

a) at least one drying device, wherein at least one drying device contains one or more infrared radiators,
b) an apparatus for generating biogas from at least one substance selected from the group consisting of waste water, process water, other residual products and any combination of two or more of these substances,
c) a line for supplying biogas from the apparatus for generating biogas to at least one of the at least one drying devices, and
d) at least one combustion gas supply line for adding a combustion gas selected from the group consisting of oxygen, air or other oxygen-containing gases to the biogas before said biogas is supplied to the at least one drying device, wherein the apparatus also comprises a waste gas line for discharging the combustion waste gas generated in the at least one infrared radiator from the at least one infrared radiator, wherein a measuring device is arranged in the waste gas line which is designed to measure the oxygen content in the waste gas resulting from the at least one infrared radiator being heated by means of the biogas, the apparatus further comprises a control unit which controls the amount of combustion gas to be supplied and added to the biogas via the supply line before said biogas is supplied to the at least one infrared radiator on the basis of the oxygen content measured by means of the measuring device, and the line is designed to supply biogas from the apparatus for generating biogas to at least one infrared radiator.

According to the invention, the at least one drying device contains one or more infrared radiators and the line is designed to supply biogas from the apparatus for generating biogas to at least one infrared radiator, i.e. the line for supplying biogas from the apparatus for generating biogas leads to or into at least one infrared radiator.

The apparatus for generating biogas is preferably a reactor which contains anaerobic microorganisms which can convert organic compounds into a methane-containing biogas.

According to a further preferred embodiment of the present invention, the apparatus further comprises at least one of the following conditioning devices:

i) one or more gas dryers for removing moisture from the biogas,
ii) one or more compressors for compressing the biogas,
iii) one or more desulphurization devices for removing sulfur-containing compounds,
iv) one or more cleaning devices containing activated carbon.

Furthermore, it is preferable for the apparatus to also comprise a buffer tank arranged in the line, in which tank biogas is temporarily stored before being used to heat the at least one infrared radiator, so as to be able to ensure continuous supply of a sufficient amount of biogas to the at least one infrared radiator even with fluctuations in the composition of the biogas and/or fluctuations in the amount of biogas generated.

According to the invention, the apparatus also comprises a waste gas line for discharging the combustion waste gas generated in the at least one infrared radiator from the at least one infrared radiator, a measuring device being arranged in the waste gas line which is designed to measure the oxygen content in the combustion waste gas generated by the at least one infrared radiator being heated by means of the biogas. The measuring device is particularly preferably a lambda sensor. As a result, the composition of the biogas used to heat the infrared radiator(s) can be adjusted by supplying combustion gas to the biogas in a manner controlled by the oxygen content in the waste gas such that effective combustion of the biogas is achieved and thus good use is made of the net calorific value of the biogas.

For this reason, according to the invention, the apparatus further comprises a control unit which controls the amount of combustion gas to be supplied and added to the biogas via the supply line before said biogas is supplied to the at least one infrared radiator on the basis of the oxygen content measured in the combustion waste gas by means of the measuring device. As a result, the composition of the biogas supplied to the infrared radiator(s) can be adjusted such that optimum combustion of the biogas and thus optimum use of the net calorific value of the biogas is achieved.

In a development of the inventive concept, the apparatus further comprises a device for determining the net calorific value of the biogas before said biogas is supplied to the at least one infrared radiator. For example, the device for determining the net calorific value of the biogas can comprise a combustion calorimeter.

In particular, it is preferable for a control unit to be contained in the apparatus, which controls the amount of biogas to be supplied to the at least one infrared radiator per unit of time and the amount of combustion gas to be supplied to the biogas per unit of time such that the at least one infrared radiator has a constant heat radiation output.

In addition, the apparatus can comprise a line for supplying natural gas into the line for supplying biogas from the apparatus for generating biogas to at least one of the at least one infrared radiators, in order to add (small amounts of) natural gas to the biogas before said biogas is supplied to the at least one infrared radiator in order to heat said at least one infrared radiator, if, for example, for production-related reasons, the amount of biogas generated in the method is temporarily too low for sufficient heating of the infrared radiators.

Furthermore, the apparatus can comprise a line for supplying methane into the line for supplying biogas from the apparatus for generating biogas to at least one infrared radiator, in order to add methane to the biogas before said biogas is supplied to the at least one infrared radiator in order to heat said at least one infrared radiator, if, for example, for production-related reasons, the net calorific value or methane content of the biogas generated in the method is temporarily too low for sufficient heating of the infrared radiators.

Figure 2:
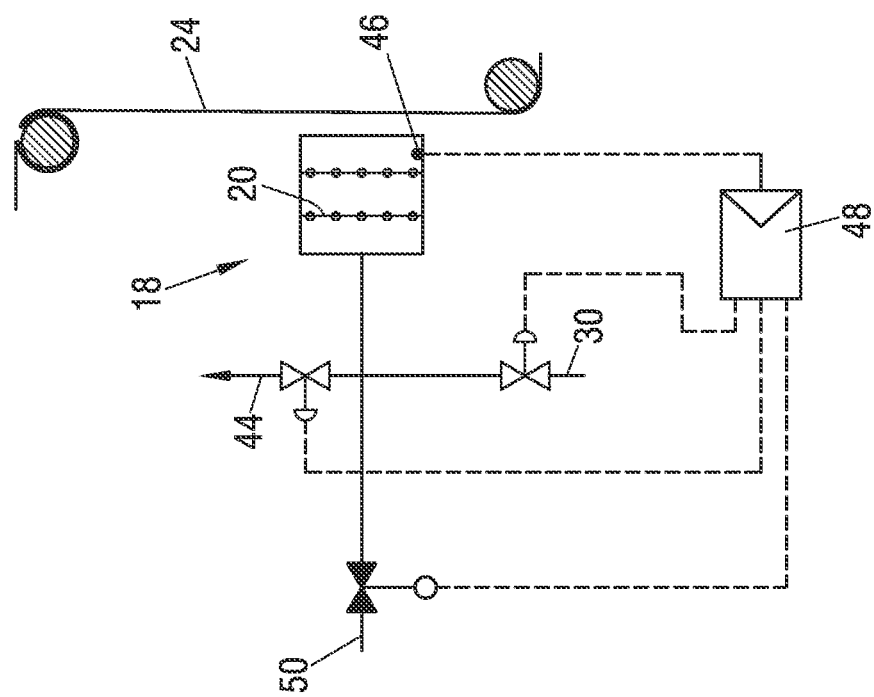

The present invention is described below with reference to figures which illustrate the invention, but do not have a limiting effect thereon, and in which FIG. 1 is a schematic view of an apparatus for producing a coated paper web according to an embodiment of the present invention, and FIG. 2 shows a schematic detail of the apparatus shown in FIG. 1, showing in detail the control of the biogas supply to the drying device.

The apparatus 10 shown in FIG. 1 for producing a coated paper web 12 comprises, as viewed in the movement direction of the web, a pulp preparation means 14, a coating machine 16 and a drying device 18, the drying device 18 containing a plurality of infrared radiators 20, each of which dries part of a material web moving through the drying device 18. A supply line 22 for waste paper leads into the pulp preparation means 14, via which line waste paper is continuously supplied to the pulp preparation means 14 during operation of the apparatus 10.

Fibrous material is generated from the waste paper in the pulp preparation means 14 after water has been supplied, by the waste paper being dissolved in the water, which fibrous material is then compacted to form the material web and coated with a coating in the coating machine 16 before the material web 24 coated in this way is dried in the drying device 18 by means of the infrared radiators 20 and thus processed to form the coated paper web 12.

Considerable amounts of water are required for the operation of the pulp preparation means 14, which water is circulated in the pulp preparation means as process water. During the operation of the pulp preparation means 14, the process water is contaminated with substances originating from the waste paper, including, for example, organic compounds. In order to clean the process water, the apparatus 10 comprises a reactor 26 containing anaerobic microorganisms, to which some of the process water is continuously supplied via the process water supply line 28. In the reactor 26, the process water is in contact with the anaerobic microorganisms, which convert the organic compounds contained in the process water as contaminants thus forming a biogas that contains methane and carbon dioxide. The biogas is withdrawn from the reactor 26 via the biogas line 30, whereas the cleaned process water is returned to the pulp preparation means 14 via the process water return line 32.

Furthermore, the apparatus 10 comprises a buffer tank 34 arranged in the biogas line 30, in which tank the biogas is temporarily stored so as to ensure continuous supply of a sufficient amount of biogas to the infrared radiators 20 even with fluctuations in the composition of the biogas and/or fluctuations in the amount of biogas generated.

In addition, for conditioning the biogas in the biogas line 30, the apparatus 10 comprises, as viewed in the flow direction, a gas dryer 36 for removing moisture from the biogas, a compressor 38 for compressing the biogas, a desulfurization device 40 for removing sulfur-containing compounds and a cleaning device 42 containing activated carbon.

Moreover, the apparatus 10 comprises a supply line 44 for combustion gas, via which air is supplied to the biogas before the gas mixture produced in this way is supplied to the infrared radiators 20 for heating purposes.

FIG. 2 shows a schematic detail of the apparatus 10 shown in FIG. 1, showing in detail the control of the biogas supply to the infrared radiators 20. According to this figure, the apparatus 10 comprises a measuring device 46, particularly preferably a lambda sensor 46, by means of which the oxygen content in the waste gas resulting from the at least one heated part 20 being heated by means of the biogas is continuously measured. In addition, the apparatus 10 comprises a control unit 48 which controls the amount of combustion gas to be supplied and added to the biogas via the supply line 44 for combustion gas before said biogas is supplied to the infrared radiators 20 on the basis of the oxygen content measured in the combustion waste gas by means of the measuring device 46. As a result, the composition of the biogas used to heat the infrared radiators 20 is adjusted such that optimum combustion of the biogas in the infrared radiators 20 and thus optimum use of the net calorific value of the biogas is achieved.

In addition, the apparatus 10 comprises a supply line for natural gas 50, which leads into the biogas line 30, in order to supply natural gas to the biogas, if required, in a manner controlled by means of the control device 48. This may be necessary if, for production-related reasons, the amount of biogas generated in the method is temporarily too low for sufficient heating of the infrared radiators 20.

LIST OF REFERENCE SIGNS 10 apparatus for producing a coated paper web
12 coated paper web
14 pulp preparation means
16 coating machine
18 drying device
20 infrared radiator
22 supply line for waste paper
24 material web
26 reactor containing anaerobic microorganisms
28 process water supply line
30 biogas line
32 process water return line
34 buffer tank
36 gas dryer
38 compressor
40 desulfurization device
42 cleaning device
44 supply line for combustion gas
46 measuring device/lambda sensor
48 control device
50 supply line for natural gas

The invention claimed is:

1. Method for producing an object, wherein the method comprises drying the object (24, 12) or a primary product thereof, the object (24, 12) or a primary product thereof being at least partially dried in at least one drying device (18), wherein at least one of the at least one drying units (18) contains at least one infrared radiator (20) which is at least partially heated by means of biogas, wherein a combustion gas selected from the group consisting of oxygen, air or other oxygen-containing gases is added to the biogas before said biogas is supplied to the at least one infrared radiator (20) in order to heat said at least one infrared radiator, and the oxygen content in the waste gas resulting from the at least one infrared radiator (20) being heated by means of the biogas is measured by means of a measuring device (46) and the amount of combustion gas added to the biogas before said biogas is supplied to the at least one infrared radiator (20) is controlled on the basis of the measured oxygen content.

2. Method according to claim 1,
wherein
waste water and/or some other residual product is also generated in the method, the biogas being produced by treating the generated waste water and/or other residual product.

3. Method according to claim 1,
wherein
the biogas contains methane.

4. Method according to claim 1,
wherein
process water is circulated during the method, which water becomes contaminated with organic compounds during the method, the biogas being produced by treating the generated process water.

5. Method according to claim 2,
wherein
waste water is generated and/or process water is circulated during the method, which process water becomes contaminated with organic compounds during the method, the treatment of the waste water and/or process water being carried out in a reactor (26) containing anaerobic microorganisms, the anaerobic microorganisms converting organic compounds contained in the waste water and/or process water into a biogas.

6. Method according to claim 2,
wherein
a residual product other than waste water and process water is generated during the method, the biogas being produced by fermenting the other residual product that has been generated.

7. Method according to claim 1,
wherein
a moving material web (24, 12) is produced by means of the method, and said web is at least partially dried in the at least one drying device (18), waste water containing organic compounds being produced and/or process water being circulated during the method, which process water becomes contaminated with organic compounds during the method, the biogas being generated by treating the waste water and/or process water in a reactor (26) containing anaerobic microorganisms, the anaerobic microorganisms converting organic compounds contained in the waster water and/or process water into the biogas.

8. Method according to claim 7,
wherein
a coated paper or cardboard web (12) is produced by means of the method.

9. Method according to claim 2,
wherein
the biogas produced contains at least 50 wt. % methane, based on 100 wt. %.

10. Method according to claim 1,
wherein
the biogas is conditioned before being used to heat the at least one infrared radiator (20), the biogas being subjected to one or more of the following treatment steps for conditioning purposes:
i) gas drying,
ii) compression,
iii) desulfurization,
iv) cleaning with activated carbon.

11. Method according to claim 1,
wherein
the biogas is temporarily stored in a buffer tank (34) before being used to heat the at least one infrared radiator (20), so as to be able to ensure continuous supply of a sufficient amount of biogas to the at least one infrared radiator (20) even with fluctuations in the composition of the biogas and/or fluctuations in the amount of biogas generated.

12. Method according to claim 1,
wherein
the measuring device (46) is a lambda sensor (46).

13. Method according to claim 1,
wherein
the net calorific value of the biogas is determined before said biogas is supplied to the at least one infrared radiator (20).

14. Method according to claim 13,
wherein
the amount of biogas to be supplied to the at least one infrared radiator (20) per unit of time is controlled on the basis of the determined net calorific value of the biogas.

15. Method according to claim 1,
wherein
the amount of biogas to be supplied to the at least one infrared radiator (20) per unit of time and the amount of combustion gas to be supplied to the biogas per unit of time are controlled such that the at least one infrared radiator (20) has a constant heat radiation output.

16. Apparatus (10) for producing an object for carrying out a method according to claim 1, wherein the apparatus comprises:
a) at least one drying device (18), wherein at least one drying device (18) contains one or more infrared radiators (20),
b) an apparatus (26) for generating biogas from at least one substance selected from the group consisting of waste water, process water, other residual products and any combination of two or more of these substances,
c) a line (30) for supplying biogas from the apparatus (26) for generating biogas to at least one of the at least one drying devices (18), and
d) at least one combustion gas supply line (44) for adding a combustion gas selected from the group consisting of oxygen, air or other oxygen-containing gases to the biogas before said biogas is supplied to the at least one drying device (18), wherein
the apparatus (10) also comprises a waste gas line for discharging the combustion waste gas generated in the at least one infrared radiator (20) from the at least one infrared radiator (20), wherein a measuring device (46) is arranged in the waste gas line which is designed to measure the oxygen content in the combustion waste gas resulting from the at least one infrared radiator (20) being heated by means of the biogas,
the apparatus (10) further comprises a control unit (48) which controls the amount of combustion gas to be supplied and added to the biogas via the supply line (44) before said biogas is supplied to the at least one infrared radiator (20) on the basis of the oxygen content measured by means of the measuring device (46), and
the line (30) is designed to supply biogas from the apparatus (26) for generating biogas to at least one infrared radiator (20).

17. Apparatus (10) according to claim 16,
wherein
the apparatus (26) for generating biogas is a reactor (26) which contains anaerobic microorganisms which can convert organic compounds into a biogas.

18. Apparatus (10) according to claim 16,
wherein
the apparatus (10) further comprises at least one of the following conditioning devices:
i) one or more gas dryers (36) for removing moisture from the biogas,
ii) one or more compressors (38) for compressing the biogas,
iii) one or more desulphurization devices (40) for removing sulfur-containing compounds,
iv) one or more cleaning devices (42) containing activated carbon.

19. Apparatus (10) according to claim 16,
wherein
the apparatus (10) also comprises a buffer tank (34) arranged in the line (30), in which tank biogas is temporarily stored before being used to heat the at least one infrared radiator (20), so as to be able to ensure continuous supply of a sufficient amount of biogas to the at least one infrared radiator (20) even with fluctuations in the composition of the biogas and/or fluctuations in the amount of biogas generated.

20. Apparatus (10) according to claim 16,
wherein
the measuring device (46) is a lambda sensor (46).

* * * * *